US00PP24694P2

(12) United States Plant Patent
Brown

(10) Patent No.: US PP24,694 P2
(45) Date of Patent: Jul. 22, 2014

(54) ***SUTERA* PLANT NAMED 'SBABB10-0'**

(50) Latin Name: *Sutera cordata*
Varietal Denomination: SBABB10-0

(71) Applicant: Graham Brown, Camden (AU)

(72) Inventor: Graham Brown, Camden (AU)

(73) Assignee: NuFlora International Pty Ltd (AU)

( * ) Notice: Subject to any disclaimer, the term of this patent is extended or adjusted under 35 U.S.C. 154(b) by 44 days.

(21) Appl. No.: 13/573,735

(22) Filed: Oct. 3, 2012

(51) Int. Cl.
*A01H 5/00* (2006.01)

(52) U.S. Cl.
USPC ..... Plt./485

(58) Field of Classification Search
USPC ..... Plt./485
See application file for complete search history.

*Primary Examiner* — Kent L Bell
(74) *Attorney, Agent, or Firm* — Cassandra Bright

(57) ABSTRACT

A new and distinct *Sutera* cultivar named 'SBABB10-0' is disclosed, characterized a trailing plant habit, flexible stems, early flowering and distinctive violet-blue flowers. The new variety is an *Sutera*, typically produced as a garden or container plant.

1 Drawing Sheet

Latin name of the genus and species: *Sutera cordata.*
Variety denomination: 'SBABB10-0'.

BACKGROUND OF THE INVENTION

The new cultivar is a product of a planned breeding program. The new variety originated from a cross pollination of the seed parent, an unnamed, unpatented proprietary selection of *Sutera cordata* with the pollen parent a different unnamed, unpatented *Sutera cordata*. The crossing was made during November of 2005, at a commercial greenhouse in New South Wales Australia. 'SBABB10-0' was discovered by the inventor, Graham Brown, a citizen of Australia, in New South Wales, at a commercial greenhouse during November of 2007.

Asexual reproduction of the new cultivar 'SBABB10-0' was first performed in New South Wales, Australia, at a commercial greenhouse by vegetative cuttings in November 2007. 'SBABB10-0' has since produced several generations and has shown that the unique features of this cultivar are stable and reproduced true to type.

SUMMARY OF THE INVENTION

The cultivar 'SBABB10-0' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SBABB10-0.' These characteristics in combination distinguish 'SBABB10-0' as a new and distinct *Sutera* cultivar:

1. Trailing plant habit.
2. Early flowering.
3. Flexible, non-brittle stems.
4. Distinctive violet-blue flowers with an orange colored tube interior.

PARENTAL COMPARISON

Plants of the new cultivar 'SBABB10-0' are similar to the female parent in most horticultural characteristics. However, the seed parent flowers three weeks later than the new variety.

Plants of the new cultivar 'SBABB10-0' are similar to the male parent in most horticultural characteristics. However, 'SBABB10-0' differs in having a trailing plant habit, whereas the pollen parent has a distinctively upright plant habit.

COMMERCIAL COMPARISON

'SBABB10-0' can be compared to the unpatented commercial variety *Sutera cordata* 'Sutcatrabl' U.S. Plant Pat. No. 17,372. Plants are similar in most horticultural characteristics, however, 'SBABB10-0' produces a flower with a larger diameter and stems that are less brittle.

BRIEF DESCRIPTION OF THE PHOTOGRAPH

The accompanying photograph in FIG. 1 illustrates in full color a typical plant of 'SBABB10-0' grown outdoors in Oxnard, Calif. This plant is approximately 2 months old, shown in a 6 inch pot. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultral Colour Chart, 2001, except where general terms of ordinary dictionary significance are used. The following observations and measurements describe 'SBABB10-0' plants in a commercial greenhouse in Oxnard, Calif. Temperatures ranged from 10° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Sutera cordata* 'SBABB10-0'.

PROPAGATION

Propagation method: Vegetative Cuttings.
Time to initiate roots: About 7 to 10 days at 20° C.

Root description: Very fine, fibrous. Colored near Yellow-White 158C.

PLANT

Growth habit: Outwardly spreading annual.
Pot size of plant described: 6 inch.
Height: Approximately 11 cm.
Plant spread: 45 cm.
Growth rate: Rapid.
Branching characteristics: Very free branching.
Length of primary lateral branches: 14 cm.
Diameter of lateral branches: 0.3 cm.
Quantity of primary lateral branches: Approximately 60.
Characteristics of primary lateral branches:
*Form*.—Round.
*Color*.—Near RHS Green 138A.
*Texture*.—Densely pubescent.
*Strength*.—Moderately strong, very flexible.
Internode length: Average 2.7 cm.

FOLIAGE

Leaf:
*Arrangement*.—Opposite.
*Quantity*.—Approximately 12 per branch.
*Average length*.—2.5 cm.
*Average width*.—2.0 cm.
*Shape of blade*.—Orbicular.
*Apex*.—Acute.
*Base*.—Cuneate.
*Margin*.—Serrate.
*Texture of top surface*.—Glabrous.
*Texture of bottom surface*.—Glabrous.
*Color*.—Young foliage upper side: Near RHS Green 137A. Young foliage under side: Near RHS Green 137B. Mature foliage upper side: Near RHS Green 137A. Mature foliage under side: Near RHS Green 137B.
*Venation*.—Type: Pinnate. Venation color upper side: Near RHS Yellow-Green 144B. Venation color under side: Near RHS Yellow-Green 144B.
*Petiole*.—Sessile.

FLOWER

Natural flowering season: Spring through Summer.
Inflorescence and flower type and habit: Single rotate flowers emerging from leaf axils.
Flower longevity on plant: Approximately 1 week.
Persistent or self-cleaning: Self-cleaning.
Bud:
*Shape*.—Puffy, elongated, irregular sphere.
*Length*.—1.4 cm.
*Diameter*.—1.1 cm.
*Color*.—Near RHS Violet N88D.
Flower size:
*Diameter*.—2.8 cm.
*Length*.—1.8 cm.
*Corolla tube diameter*.—0.4 cm.
Corolla/petals:
*Arrangement*.—Rotate.
*Petal quantity*.—5.
*Lobe length*.—1.2 cm.
*Lobe width*.—1.3 cm.
*Texture*.—Glabrous.
*Lobe apex*.—Obtuse.
*Lobe shape*.—Orbicular.
*Margin*.—Entire.
*Aspect*.—Concave.
*Tube length*.—0.7 cm.
*Tube texture*.—Exterior glabrous, interior pubescent.
*Color*.—When opening: Upper surface: Near RHS Violet N88D. Lower surface: Near RHS Violet-Blue 91B. Fully opened: Upper surface: Near RHS Violet-Blue 91B. Lower surface: Near RHS Violet-Blue 91C. Outer Corolla tube color: Near RHS Yellow-Orange 22B. Inner Corolla tube color: Near RHS Orange N25B.
Calyx/sepals:
*Quantity per flower*.—5.
*Shape*.—Linear.
*Length*.—0.6 cm.
*Width*.—0.15 cm.
*Apex*.—Acute.
*Base*.—Fused.
*Margin*.—Entire.
*Texture*.—Pubescent.
*Color*.—Upper Surface: Near RHS Green 137A. Lower Surface: Near RHS Green 137A.
Peduncle:
*Length*.—Approximately 1.8 cm.
*Diameter*.—Approximately 0.1 cm.
*Color*.—Near RHS Green 137A.
*Orientation*.—Approximately 45 degree angle from leaf axil.
*Pubescence*.—Pubescent.
Fragrance: None.

REPRODUCTIVE ORGANS

Stamens:
*Number*.—4.
*Filament length*.—Approximately 0.7 cm.
Anthers:
*Shape*.—Globular.
*Length*.—Approximately 0.1 cm.
*Color*.—Near RHS Greyed-Orange 163B.
*Pollen*.—Color: Near RHS Yellow-Orange 23B. Quantity: Moderate.
Pistil:
*Number*.—1.
*Length*.—Approximately 1.3 cm.
*Style*.—Length: 1.2 cm. Color: Near RHS Yellow-Green 150D.
*Stigma*.—Shape: linear. Color: Near RHS Yellow 6A. Ovary Color: RHS Green 143B.

OTHER CHARACTERISTICS

Seeds and fruits: Not observed to date.
Disease/pest resistance: Neither resistance nor susceptibility to normal diseases and pests of *Sutera* has been observed.
Temperature tolerance: Tolerates temperatures from approximately −1° C. to 35° C.
Drought tolerance: No tolerance for drought.

What is claimed is:

1. A new and distinct cultivar of *Sutera* plant named 'SBABB10-0' as herein illustrated and described.

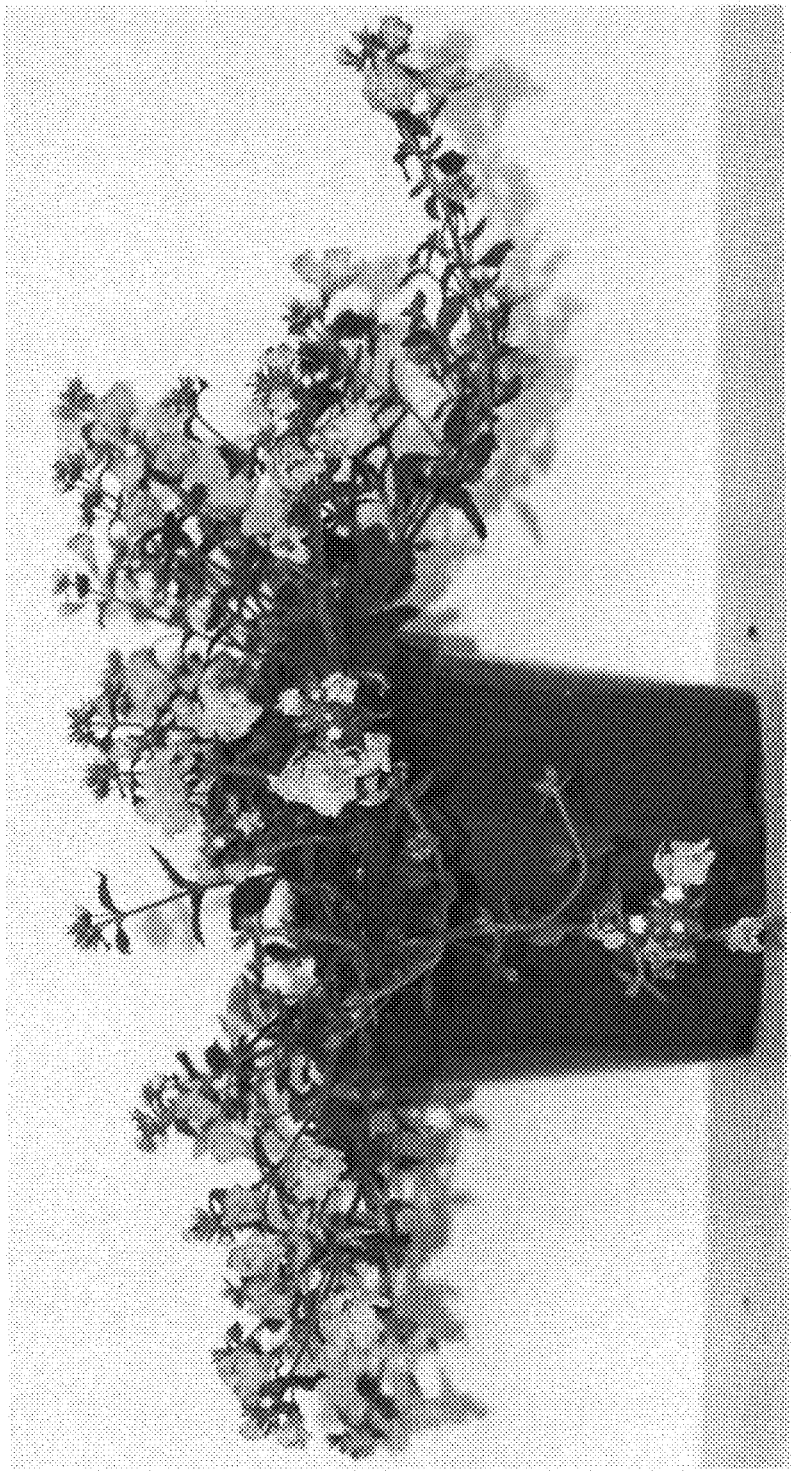

* * * * *